United States Patent
Dewey

(10) Patent No.: US 11,571,313 B2
(45) Date of Patent: Feb. 7, 2023

(54) SPINAL IMPLANT SYSTEM AND METHOD

(71) Applicant: WARSAW ORTHOPEDIC INC., Warsaw, IN (US)

(72) Inventor: Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 162 days.

(21) Appl. No.: 17/209,409

(22) Filed: Mar. 23, 2021

(65) Prior Publication Data

US 2021/0330471 A1 Oct. 28, 2021

Related U.S. Application Data

(60) Provisional application No. 63/014,956, filed on Apr. 24, 2020.

(51) Int. Cl.
  *A61F 2/44* (2006.01)
  *A61F 2/46* (2006.01)
  *A61F 2/30* (2006.01)

(52) U.S. Cl.
  CPC .. *A61F 2/4425* (2013.01); *A61F 2002/30523* (2013.01); *A61F 2002/30574* (2013.01); *A61F 2002/30617* (2013.01); *A61F 2002/443* (2013.01)

(58) Field of Classification Search
  CPC .......... A61F 2/4425; A61F 2/44; A61F 2/442; A61F 2/4455; A61F 2/4611; A61F 2002/30523; A61F 2002/30574; A61F 2002/30617; A61F 2002/443

USPC ............................................ 623/17.11–17.16
  See application file for complete search history.

(56) References Cited

U.S. PATENT DOCUMENTS

| | | | | |
|---|---|---|---|---|
| 7,674,296 B2* | 3/2010 | Rhoda | ..................... | A61F 2/442 623/17.11 |
| 7,691,147 B2* | 4/2010 | Gutlin | ..................... | A61F 2/44 606/90 |
| 7,819,922 B2* | 10/2010 | Sweeney | ..................... | A61F 2/44 623/17.15 |
| 7,909,870 B2* | 3/2011 | Kraus | ..................... | A61F 2/4611 623/17.11 |
| 8,152,852 B2* | 4/2012 | Biyani | ..................... | A61F 2/44 623/17.16 |
| 8,182,537 B2* | 5/2012 | Refai | ..................... | A61F 2/44 623/17.16 |

(Continued)

*Primary Examiner* — Jessica Weiss
(74) *Attorney, Agent, or Firm* — Sorell, Lenna & Schmidt, LLP

(57) ABSTRACT

A spinal implant includes a first member that is curved along an axis between opposite ends. The first member defines a bore and a first thread. A second member is positioned in the bore and is curved between opposite ends. The second member includes a second thread engaged with the first thread. The second thread includes a series of gear teeth. A third member is positioned in the bore and is curved between opposite ends and includes opposite ends. A driver includes a gear configured to engage the gear teeth such that rotation of the driver relative to the first member and the second member rotates the second member relative to the first member to translate the second member relative to the first member along the axis. Systems and methods are disclosed.

20 Claims, 5 Drawing Sheets

(56) References Cited

U.S. PATENT DOCUMENTS

| | | | | |
|---|---|---|---|---|
| 8,282,683 B2* | 10/2012 | McLaughlin | ......... | A61F 2/4455 |
| | | | | 623/17.11 |
| 11,452,612 B2* | 9/2022 | Stinchfield | ............ | A61F 2/4465 |
| 2005/0060037 A1* | 3/2005 | Michelson | ............ | A61F 2/4455 |
| | | | | 623/17.15 |
| 2005/0090898 A1* | 4/2005 | Berry | ........................ | A61F 2/44 |
| | | | | 623/17.11 |
| 2006/0100710 A1* | 5/2006 | Gutlin | ........................ | A61F 2/44 |
| | | | | 623/17.15 |

* cited by examiner

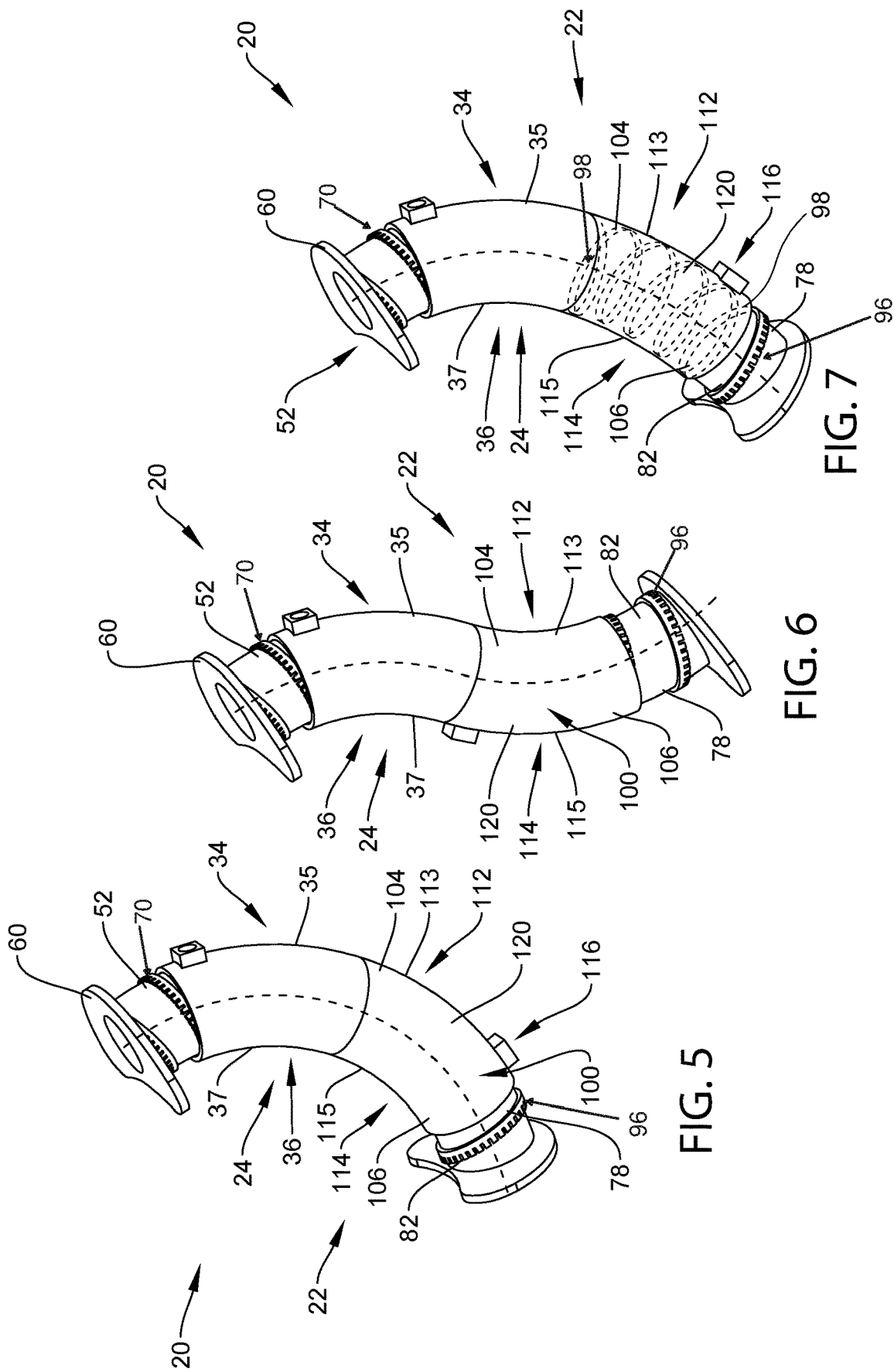

SPINAL IMPLANT SYSTEM AND METHOD

TECHNICAL FIELD

The present disclosure generally relates to medical devices for the treatment of musculoskeletal disorders, and more particularly to a spinal construct configured for disposal with spaced vertebrae and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, corpectomy, discectomy, laminectomy and implantable prosthetics. In procedures, such as, for example, corpectomy and discectomy, fusion and fixation treatments may be performed that employ implants to restore the mechanical support function of vertebrae.

Furthermore, it is noted that there is an increasing need for polyetheretherketone (PEEK) based expandable corpectomy devices. However, since PEEK is weaker than other materials, such as, for example, titanium or stainless steel, PEEK based expandable corpectomy devices tend to break under high load scenarios, such as, for example, when the devices bear anatomical loads. This disclosure describes an improvement over these prior technologies.

SUMMARY

In one embodiment, a spinal implant is provided. The spinal implant includes a first member extending along a longitudinal axis between opposite first and second ends. The first member is curved along the longitudinal axis from the first end to the second end. The first member comprises an inner surface. The inner surface defines a bore and a first thread. A second member comprises opposite proximal and distal ends. The second member is curved from the proximal end to the distal end. The distal end is positioned in the bore. The proximal end comprises an end plate. The second member comprises a second thread engaged with the first thread. The second thread comprises a series of gear teeth. A third member comprises opposite proximal and distal ends. The third member is curved from the proximal end of the third member to the distal end of the third member. The proximal end of the third member is positioned in the bore. The distal end of the third member comprises an end plate. A driver comprises a gear configured to engage the gear teeth such that rotation of the driver relative to the first member and the second member rotates the second member relative to the first member to translate the second member relative to the first member along the longitudinal axis.

In one embodiment, a spinal implant is provided. The spinal implant includes a first member extending along a longitudinal axis between opposite first and second ends. The first member is curved along the longitudinal axis from the first end to the second end. The first member comprises an inner surface. The inner surface defines a bore and a first thread. A second member comprises opposite proximal and distal ends. The second member is curved from the proximal end to the distal end. The distal end is positioned in the bore. The proximal end comprises an end plate. The second member comprises a second thread engaged with the first thread. The second thread comprises a series of gear teeth. A third member comprises opposite proximal and distal ends. The third member is curved from the proximal end of the third member to the distal end of the third member. The proximal end of the third member is positioned in the bore. The distal end of the third member comprises an end plate. A driver comprises a gear configured to engage the gear teeth such that rotation of the driver relative to the first member and the second member rotates the second member relative to the first member to translate the second member relative to the first member along the longitudinal axis. A collar is positioned about a sleeve of the third member. The collar comprises a third thread. The sleeve comprises a fourth thread engaged with the third thread. The fourth thread comprises a series of gear teeth configured to engage the gear such that rotation of the driver relative to the collar and the third member rotates the collar relative to the third member to translate the collar relative to the third member along the longitudinal axis. The third member moves between a first orientation in which the proximal end of the third member is positioned within the second member and a second orientation in which the third member is spaced apart from the second member as the second member translates relative to the first member along the longitudinal axis.

In one embodiment, a spinal implant is provided. The spinal implant includes a first member extending along a longitudinal axis between opposite first and second ends. The first member is curved along the longitudinal axis from the first end to the second end. The first member comprises an inner surface. The inner surface defines a bore and a first thread. A second member comprises opposite proximal and distal ends. The second member is curved from the proximal end to the distal end. The distal end is positioned in the bore. The proximal end comprises an end plate. The second member comprises a second thread engaged with the first thread. The second thread comprises a series of gear teeth. A third member comprises opposite proximal and distal ends. The third member is curved from the proximal end of the third member to the distal end of the third member. The proximal end of the third member is positioned in the bore. The distal end of the third member comprises an end plate. A driver comprises a gear configured to engage the gear teeth such that rotation of the driver relative to the first member and the second member rotates the second member relative to the first member to translate the second member relative to the first member along the longitudinal axis. A collar is positioned about a sleeve of the third member. The collar comprises a third thread. The sleeve comprises a fourth thread engaged with the third thread. The fourth thread comprises a series of gear teeth configured to engage the gear such that rotation of the driver relative to the collar and the third member rotates the collar relative to the third member to translate the collar relative to the third member along the longitudinal axis. The longitudinal axis is a first longitudinal axis. The third member extends along a second longitudinal axis from the proximal end of the third member to the distal end of the third member. The third member moves from a first orientation to a second orientation as the collar translates relative to the third member along the first longitudinal axis. The collar has a first radius of curvature when the third member is in the first orientation and a second radius of curvature when the third member is in the second orientation. The second radius of curvature is different than the first radius of curvature. The second member extends along a third longitudinal axis from the proximal end of the second member to the distal end of the second member. The second member moves from a third orientation to a fourth orientation as the second member translates relative to the first member along the first longitudinal axis. The second member has a third radius of curvature when the second member is in the third orientation and a fourth radius of curvature when the second member is in the fourth orientation, the fourth radius of curvature being different than the third radius of curvature.

BRIEF DESCRIPTION OF THE DRAWINGS

The present disclosure will become more readily apparent from the specific description accompanied by the following drawings, in which:

FIG. 5 is a perspective view of components of the system shown in FIG. 1;

FIG. 6 is a perspective view of components of the system shown in FIG. 1;

FIG. 7 is a perspective view of components of the system shown in FIG. 1; and

DETAILED DESCRIPTION

Figure 1:
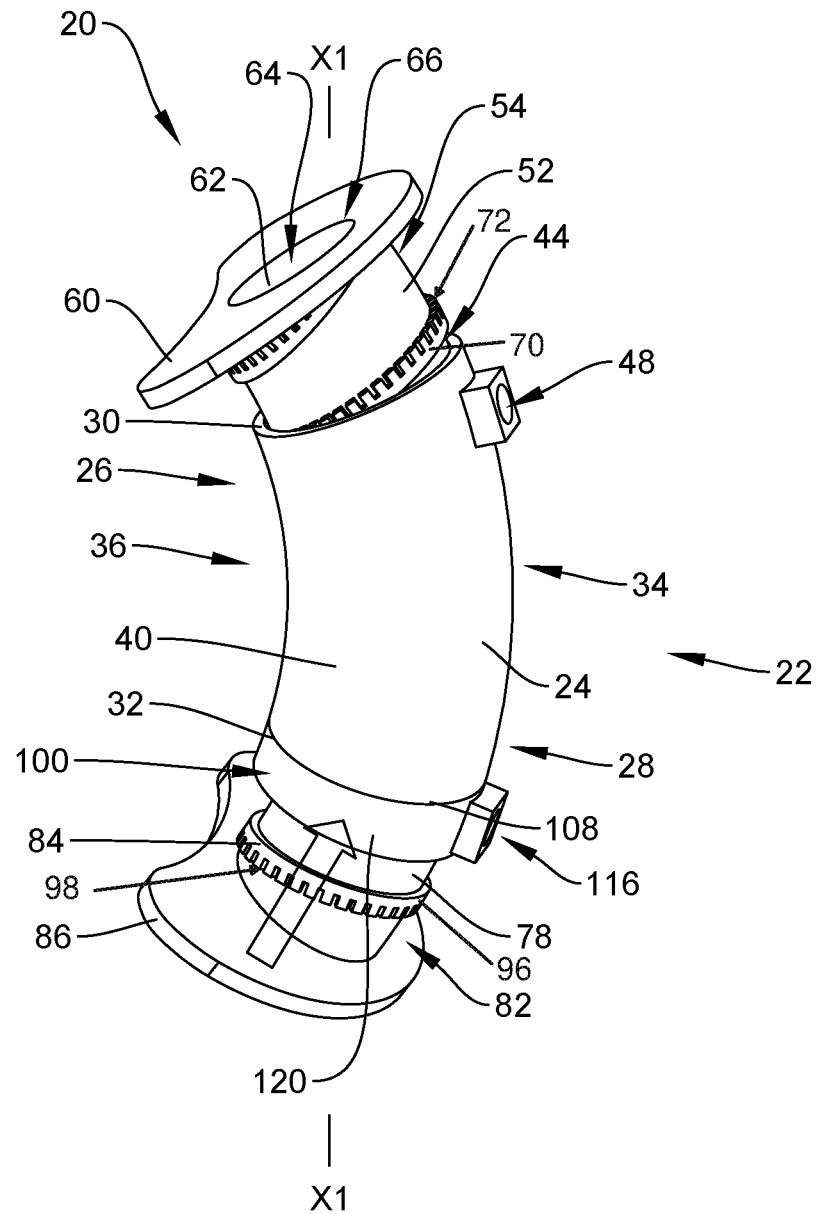
FIG. 1 is a perspective view of components of one embodiment of a spinal implant system in accordance with the principles of the present disclosure.
Figure 2:
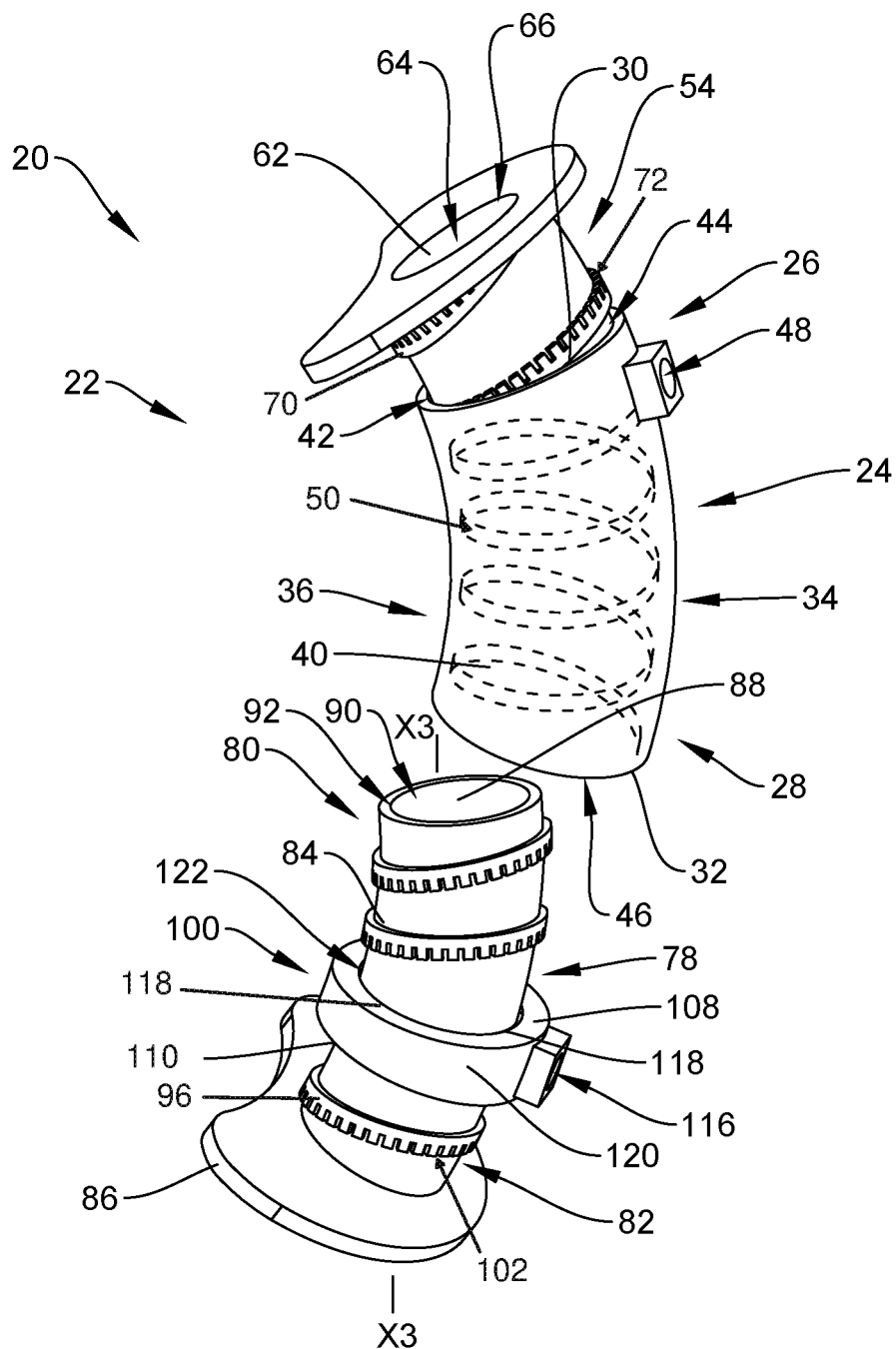
FIG. 2 is a perspective view of components of the system shown in FIG. 1.

The exemplary embodiments of a surgical system and related methods of use disclosed are discussed in terms of medical devices for the treatment of musculoskeletal disorders and more particularly, in terms of a spinal implant system that includes an expandable interbody implant configured for disposal with spaced vertebrae and a method for treating a spine.

In some embodiments, the spinal implant system includes expandable corpectomy implants that allow combination of curvatures, pairing of opposing curvatures (TL juncture), as well as a nested version with additional expansion in the same size implant.

In some embodiments, the spinal implant system includes expandable corpectomy implants that introduce modularity to open up additional benefits of one or more implants or cages that can expand along a lordotic curve. In some embodiments, the cages expand along a lordotic curve by combining two cages to increase the amount of expansion of the implanted device. In some embodiments, at least one of the cages combines a concave curvature with a convex curvature to bridge the TL juncture and/or avoid anatomy. In some embodiments, at least one of the cages combines a tight curvature with a flat curvature for different expansion characteristics than a single-curvature cage. In some embodiments, at least one of the cages nests inside another one of the cages to gain twice the expansion with a modestly larger collapsed cage. In some embodiments, at least one of the cages includes a thread that can be bent around an angle of lordosis.

In some embodiments, the implant includes a first cage and a second cage, wherein the second cage is used to increase the total amount of distraction of the implant. In some embodiments, the implant includes opposing curves (concave and convex) that are combined to conform to or avoid anatomy and/or fit the surgical site better (such as at the thoracolumbar juncture).

In some embodiments, the implant includes a top part and a bottom part, wherein the bottom part includes an inner piece that is sized to nest within an inner piece of the top part to give additional expansion with a modest increase in overall collapsed implant height. In some embodiments, one of the inner pieces nests inside the other inner piece to maximize expansion while maintaining implant insertion size. In some embodiments, the outer piece of the top part has a close fit with the inner piece of the top part to provide support during expansion. In some embodiments, the outer piece of the bottom part has a close fit with the inner piece of the bottom part to support it. In some embodiments, at least one of the inner pieces is flexible. In some embodiments, the curvature of the first part is the same as the curvature of the second part. In some embodiments, the curvature of the first part is different than the curvature of the second part. In some embodiments, the implant is provided in one piece. In some embodiments, the implant is provided with the implant assembled.

In some embodiments, any type of fastening feature could be used between the modular components (detents, adhesive, threads, etc.). In some embodiments, the implant can be assembled on the back table or in situ, or be provided already assembled from the manufacturer. In some embodiments, the implant may start in a fully collapsed position and is then expanded to space bones (or anatomy) apart. In some embodiments, the implant may start in a fully expanded position and is then collapsed to pull two bones (or anatomy) together. In some embodiments, the implant could include endplates with holes for anchors to fix the endplates/implant to adjacent structures. In some embodiments, the implant has curvature in the same plane. In some embodiments, the curvature of the implant can be combined off-planar if needed per procedure. In some embodiments, the system includes two devices. In some embodiments, the system includes more than two devices.

In one embodiment, one or all of the components of the spinal implant system are disposable, peel-pack, pre-packed sterile devices used with an implant. One or all of the components of the spinal implant system may be reusable. The spinal implant system may be configured as a kit with multiple sized and configured components.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor, infection, such as, for example, tuberculosis, and fractures. In some embodiments, the present disclosure may be employed with other osteal and bone related applications, including those associated with diagnostics and therapeutics. In some embodiments, the disclosed spinal implant system and methods may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system and methods of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system and related methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-8, there is illustrated components of a surgical system, such as, for example, a spinal implant system 20.

The components of spinal implant system 20 can be fabricated from biologically acceptable materials suitable for medical applications, including metals, synthetic polymers, ceramics and bone material and/or their composites. For example, the components of spinal implant system 20, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 20 may have material composites, including the above materials, to achieve various desired characteristics such as strength, rigidity, elasticity, compliance, biomechanical performance, durability and radiolucency or imaging preference. The components of spinal implant system 20, individually or collectively, may also be fabricated from a heterogeneous material such as a combination of two or more of the above-described materials. The components of spinal implant system 20 may be monolithically formed, integrally connected or include fastening elements and/or instruments, as described herein.

Spinal implant system 20 is employed, for example, with a minimally invasive procedure, including percutaneous techniques, mini-open and open surgical techniques to deliver and introduce instrumentation and/or an implant, such as, for example, a corpectomy implant, at a surgical site within a body of a patient, for example, a section of a spine. In some embodiments, spinal implant system 20 may be employed with surgical procedures, such as, for example, corpectomy and discectomy, which include fusion and/or fixation treatments that employ implants, to restore the mechanical support function of vertebrae.

Spinal implant system 20 includes an expandable interbody implant 22. In some embodiments, implant 22 includes an outer body, such as, for example, a member 24 extending along a longitudinal axis X1 between opposite a proximal end 26 and an opposite distal end 28. Member 24 is pre-formed to be curved along axis X1 from end 26 to end 28. End 26 includes an end surface 30 and end 28 includes an end surface 32 opposite surface 30. Surfaces 30, 32 each extend at an acute angle relative to axis X1. Member 24 includes an anterior end 34 and an opposite posterior end 36. In some embodiments, end 34 is convexly curved from surface 30 to surface 32 and end 36 is concavely curved from surface 30 to surface 32. In some embodiments, end 34 is continuously curved from surface 30 to surface 32 and end 36 is continuously curved from surface 30 to surface 32. In some embodiments, end 34 has a radius of curvature that is less than a radius of curvature of end 36. In some embodiments, end 34 is concavely curved from surface 30 to surface 32 and end 36 is convexly curved from surface 30 to surface 32. In some embodiments, end 34 has a radius of curvature that is greater than a radius of curvature of end 36. In some embodiments, surface 30 and/or surface 34 extend at an acute angle relative to axis X1.

Member 24 includes an inner surface 38 an opposite outer surface 40. Surface 38 defines a bore 42 that extends along an entire length of member 24. Bore 42 is continuously curved from end 26 to end 28 and/or from surface 30 to surface 32. End 26 includes an opening 44 extending through surface 30 and end 28 includes an opening 46 extending through surface 32. In some embodiments, bore 42, opening 44 and/or opening 46 may have various cross section configurations, such as, for example, circular, oval, oblong, triangular, rectangular, square, polygonal, irregular, uniform, non-uniform, variable, tubular and/or tapered. Member 24 includes a port 48 extending through surfaces 38, 40 such that port 48 is in communication with bore 42. Surface 38 defines a helical thread, such as, for example, thread 50. In some embodiments, thread 50 extends continuously from end 26 to end 28 and/or from surface 30 to surface 32. It is noted that thread 50 is omitted in certain figures in order to provide clarity.

Implant 22 includes a proximal member, such as, for example a member 52 extending along a longitudinal axis X2 between a proximal end 54 and an opposite distal end 56. In some embodiments, member 52 is pre-formed such that member 52 is continuously curved from end 54 to end 56 along axis X2. In some embodiments, member 52 is movable between a first orientation in which member 52 is linear or substantially linear from end 54 to end 56 along axis X2 to a second orientation in which member 52 is curved from end 54 to end 56 along axis X2. That is, member 52 bends along axis X2 as member 52 transitions between the first and second orientations. For example, in some embodiments, ends 54, 56 extend perpendicular to axis X2 when member 52 is in the first orientation and at least one of ends 54, 56 extend at an acute angle relative to axis X2 when member 52 is in the second orientation. End 56 is configured to be positioned in bore 42 such that an outer surface 58 of member 52 slidingly engages surface 38. End 54 comprises an end plate 60. In some embodiments, end plate 60 extends perpendicular to axis X2 when member 52 is in the first orientation and extends at an acute angle relative to axis X2 when member 52 is in the second orientation. In some embodiments, end plate 60 extends at an acute angle relative to axis X2 when member 52 is in the first orientation and the second orientation.

Member 52 includes an inner surface 62 opposite surface 58. Surface 62 defines a passageway 64 that extends the entire length of member 52. End 54 includes an opening 66 that is in communication with passageway 64 and end 56 includes an opening 68 that is in communication with passageway 64. Surface 62 defines a helical male thread 70 configured to engage thread 50. Thread 70 includes a series of gear teeth 72 configured to engage a gear 74 of a driver 76 such that rotation of driver 76 relative to members 24, 52 rotates member 52 relative to member 24 such that member 52 translates relative to member 24 along axis X1, as discussed herein. It is noted that thread 70 is omitted from certain figures in order to provide clarity. In some embodiments, member 52 bends along axis X2 as member 52 translates relative to member 24 along axis X1 such that member 52 has a radius of curvature that is equal to a radius of curvature of member 24 as member 52 translates relative to member 24 along axis X1. In some embodiments, passageway 64, opening 66 and/or opening 68 may have various cross section configurations, such as, for example, circular, oval, oblong, triangular, rectangular, square, polygonal, irregular, uniform, non-uniform, variable, tubular and/or tapered.

Implant 22 includes a sleeve or distal member, such as, for example a member 78 extending along a longitudinal axis X3 between a proximal end 80 and an opposite distal end 82. In some embodiments, member 78 is pre-formed to be continuously curved from end 80 to end 82 along axis X3. In some embodiments, member 78 is movable between a first configuration in which member 78 is linear or substantially linear from end 80 to end 82 along axis X3 to a second configuration in which member 78 is curved from end 80 to end 82 along axis X3. That is, member 78 bends along axis X3 as member 78 transitions between the first and second configurations. For example, in some embodiments, ends 78, 80 extend perpendicular to axis X3 when member 78 is in the first configuration and at least one of ends 78, 80 extend at an acute angle relative to axis X3 when member 78 is in the second configuration. End 80 is configured to extend through opening 68 to be positioned in passageway 64 such that an outer surface 84 of member 78 slidingly engages surface 62. End 82 comprises an end plate 86. In some embodiments, end plate 82 extends perpendicular to axis X3 when member 78 is in the first configuration and extends at an acute angle relative to axis X3 when member 78 is in the second configuration. In some embodiments, end plate 78 extends at an acute angle relative to axis X3 when member 78 is in the first configuration and the second configuration.

Member 78 includes an inner surface 88 opposite surface 84. Surface 88 defines a passageway 90 that extends the entire length of member 78. End 80 includes an opening 92 that is in communication with passageway 90. In some embodiments, end 82 includes an opening that is in communication with passageway 90. Surface 84 defines a helical male thread 96 configured to engage a helical female thread 98 of a collar 100 of implant 22. Thread 96 includes a series of gear teeth 102 configured to engage gear 74 such that rotation of driver 76 relative to member 78 and collar 100 rotates collar 100 relative to member 78 such that collar 100 translates relative to member 78 along axis X3, as discussed herein. It is noted that threads 96, 98 are omitted from certain figures in order to provide clarity. In some embodiments, passageway 90 and/or opening 92 may have various cross section configurations, such as, for example, circular, oval, oblong, triangular, rectangular, square, polygonal, irregular, uniform, non-uniform, variable, tubular and/or tapered. In some embodiments, collar 100 is movable relative to member 24 between a configuration in which surface 108 directly engages surface 32 and a configuration in which surface 108 is spaced apart from surface 32. In some embodiments, collar 100 is integrally and/or monolithically formed with member 24. In some embodiments, member 78 bends along axis X3 as collar 100 translates relative to member 78 along axis X3 such that member 78 has a radius of curvature that is equal to a radius of curvature of collar 100 as collar 100 translates relative to member 78 along axis X3.

Collar 100 extends along a longitudinal axis X4 between a proximal end 104 and an opposite distal end 116. In some embodiments, collar 100 is pre-formed to be curved along axis X4 from end 104 to end 106. End 104 includes an end surface 108 and end 106 includes an end surface 110 opposite surface 108. Surface 108 directly engages surface 32. Surfaces 108, 110 each extend at an acute angle relative to axis X4. It is envisioned that collar 100 can be provided with a variety of different heights and curvatures. For example, in one embodiment, shown in FIGS. 1-4, collar 100 has a first height and first curvature, and in another embodiment, shown in FIGS. 5-7, collar 100 has an increased second height and an increased second curvature. In some embodiments, the height and/or curvature of member 24 can also be selectively modified such that the height and/or curvature of member 24 can be selected to conform to a first portion of anatomy and the height and/or curvature of collar 100 can be selected to conform to a second portion of anatomy. In some embodiments, the height and/or curvature of member 24 can also be selectively modified such that the height and/or curvature of member 24 can be selected to avoid a first portion of anatomy and the height and/or curvature of collar 100 can be selected to avoid a second portion of anatomy.

Collar 100 includes an anterior end 112 and an opposite posterior end 114. In some embodiments, end 112 is convexly curved from surface 108 to surface 110 and end 114 is concavely curved from surface 108 to surface 110. In some embodiments, end 112 is continuously curved from surface 108 to surface 110 and end 114 is continuously curved from surface 108 to surface 110. In some embodiments, end 112 has a radius of curvature that is less than a radius of curvature of end 114. In some embodiments, end 112 is concavely curved from surface 108 to surface 110 and end 114 is convexly curved from surface 108 to surface 110. In some embodiments, end 112 has a radius of curvature that is greater than a radius of curvature of end 114. Collar 100 includes a port 116 extending through an inner surface 118 of collar 100 and an opposite outer surface 120 of collar 100 such that port 116 is in communication with a channel 122 of collar 100 that is defined by surface 118. Surface 118 further defines thread 98. In some embodiments, member 24 and collar 100 provide implant 22 with opposing curves (concave and convex), as shown in FIG. 6, to conform to anatomy or fit better within a surgical site, such as, for example, a thoracolumbar juncture. In some embodiments, member 24 and collar 100 provide implant 22 with a standard radius curve that can be combined with a flatter curve, as shown in FIG. 7, to suit the anatomy. In some embodiments, member 24 and collar 100 provide implant 22 with a flat curve such that implant 22 is a straight implant, wherein translation of member 50 relative to member 24 and/or translation of member 78 relative to collar 100 independent of the lordosis.

In some embodiments, collar 100 is coupled to member 24 such that an outer surface 35 of end 34 is continuous with an outer surface 113 of end 112 and an outer surface 37 of end 36 is continuous with an outer surface 115 of end 114, as shown in FIGS. 5-7, for example. In some embodiments, surface 35 has a radius of curvature that is equal to a radius of curvature of surface 113 and/or surface 37 has a radius of curvature that is equal to a radius of curvature of surface 115. In some embodiments, surface 35 has a radius of curvature that is less than a radius of curvature of surface 113 and/or surface 37 has a radius of curvature that is less than a radius of curvature of surface 115. In some embodiments, surface 35 has a radius of curvature that is greater than a radius of curvature of surface 113 and/or surface 37 has a radius of curvature that is greater than a radius of curvature of surface 115.

Driver 76 includes a handle 124 and a shaft 126 configured to fit through ports 48, 116. Shaft 126 extends along a longitudinal axis X5 between an end 128 and an opposite end 130. Handle 124 is coupled to end 128 to provide torsion. End 130 includes gear 74.

Figure 3:
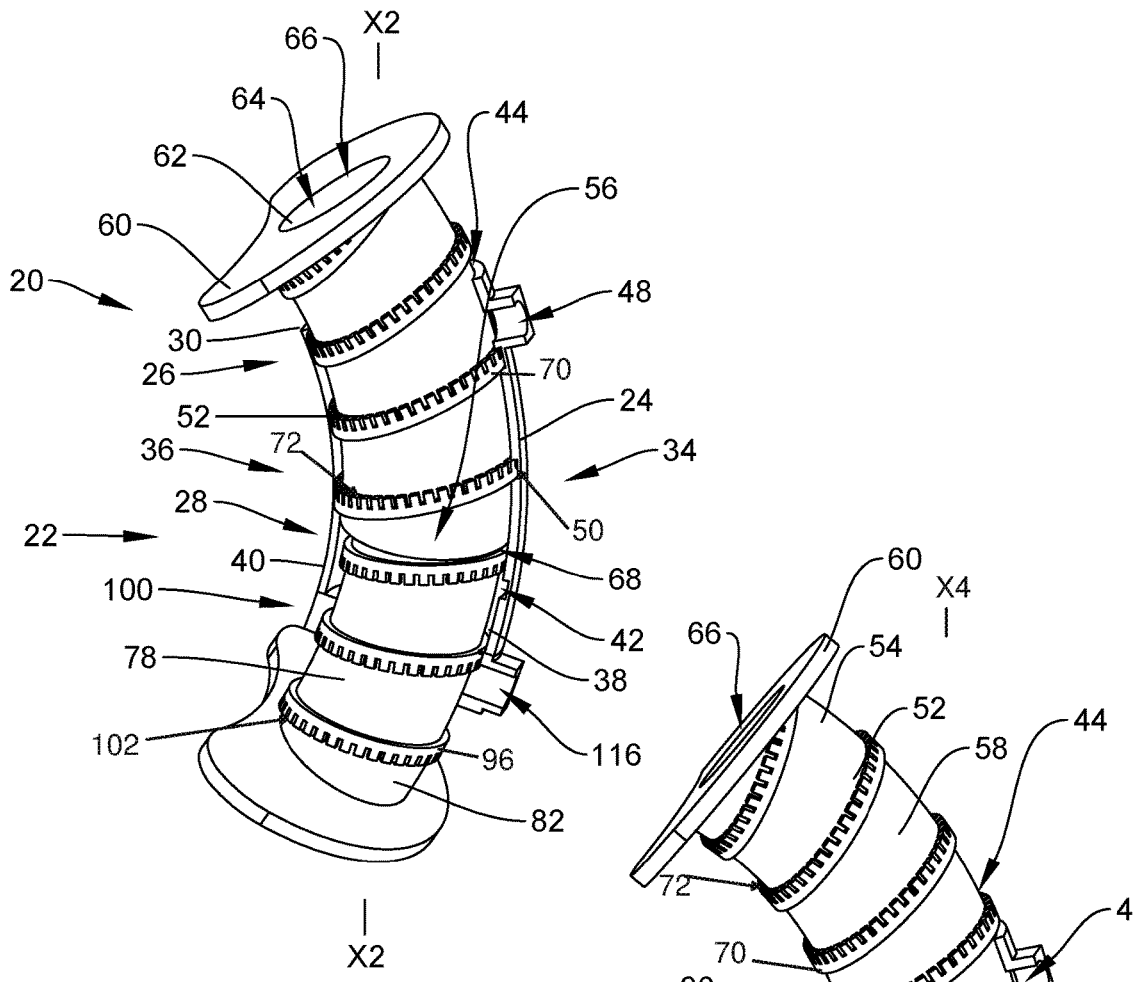
FIG. 3 is a perspective view, in part cross-section, of components of the system shown in FIG. 1.
Figure 4:
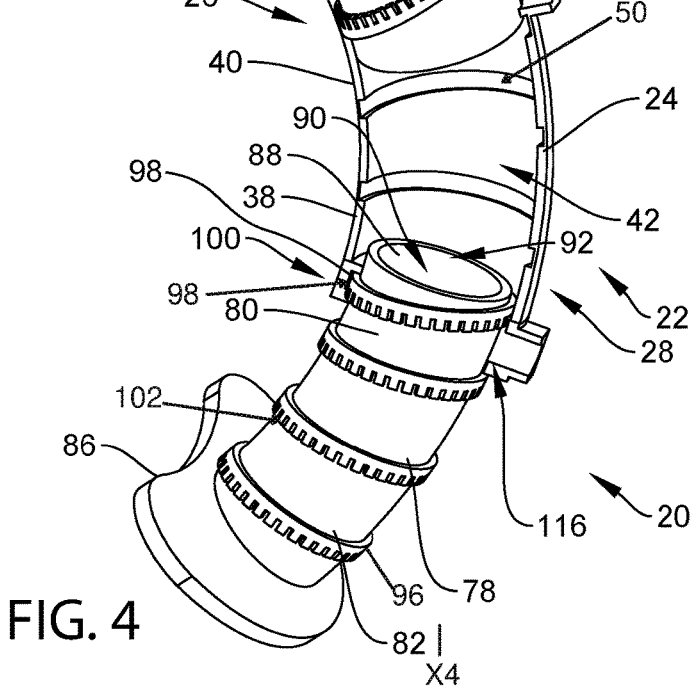
FIG. 4 is a perspective view, in part cross-section, of components of the system shown in FIG. 1.
Figure 8:
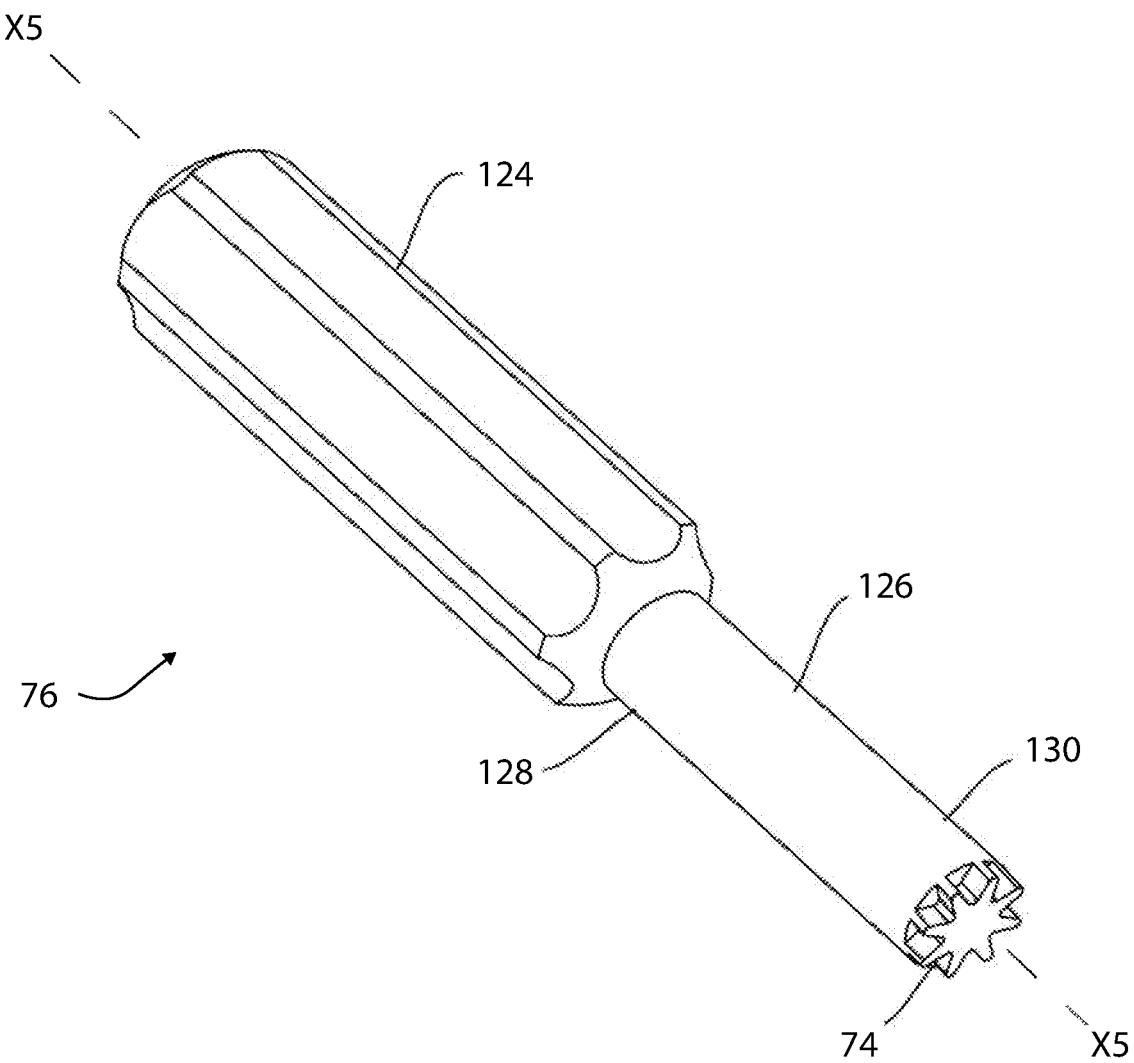
FIG. 8 is a perspective view of a component of the system shown in FIG. 1.

In order to move implant 22 from a collapsed or non-expanded orientation, shown in FIG. 3, to an expanded orientation, shown in FIG. 4, member 52 is translated relative to member 24 by inserting end 130 into port 48 such that gear 74 engages teeth 72. Driver 74 is rotated about axis X5 in a first rotational direction, such as, for example, clockwise to rotate member 52 relative to member 24 such that thread 70 moves within thread 50 to translate member 52 relative to member 24 along axis X1 in the direction shown by arrow A in FIG. 4. End 130 is then removed from port 48 and is inserted into port 116 such that gear 74 engages teeth 102. Driver 74 is rotated about axis X5 in the first rotational direction to rotate collar 100 relative to member 78 such that thread 96 moves within thread 98 to translate member 78 relative to collar 100 in the direction shown by arrow B in FIG. 4. In some embodiments, end 80 is positioned in passageway 64 when implant 22 is in the collapsed or non-expanded orientation, shown in FIG. 3, and member 78 spaced apart from member 52 when implant 22 is in the expanded orientation, shown in FIG. 4. This provides added strength to implant 22 when implant 22 is in the collapsed or non-expanded orientation.

In order to move implant 22 from the expanded orientation, shown in FIG. 4, to the collapsed or non-expanded orientation, shown in FIG. 3, member 52 is translated relative to member 24 by inserting end 130 into port 48 such that gear 74 engages teeth 72. Driver 74 is rotated about axis X5 in an opposite rotational direction, such as, for example, counterclockwise to rotate member 52 relative to member 24 such that thread 70 moves within thread 50 to translate member 52 relative to member 24 along axis X1 in the direction shown by arrow B in FIG. 4. End 130 is then removed from port 48 and is inserted into port 116 such that gear 74 engages teeth 102. Driver 74 is rotated about axis X5 in the second rotational direction to rotate collar 100 relative to member 78 such that thread 96 moves within thread 98 to translate member 78 relative to collar 110 in the direction shown by arrow A in FIG. 4.

In assembly, operation and use, spinal implant system 20, similar to the systems and methods described herein, and including implant 22 is employed with a surgical procedure, such as, for example, a lumbar corpectomy for treatment of a spine of a patient including vertebrae. Spinal implant system 20 may also be employed with other surgical procedures, such as, for example, discectomy, laminectomy, fusion, laminotomy, laminectomy, nerve root retraction, foramenotomy, facetectomy, decompression, spinal nucleus or disc replacement and bone graft and implantable prosthetics including vertebral replacement devices, interbody devices, plates, rods, and bone engaging fasteners for securement of the components of implant 22.

Spinal implant system 20 is employed with a lumbar corpectomy including surgical arthrodesis, such as, for example, fusion to immobilize a joint for treatment of an applicable condition or injury of an affected section of a spinal column and adjacent areas within a body. In some embodiments, implant 22 is configured for insertion within a vertebral space to space apart articular joint surfaces, provide support and maximize stabilization of vertebrae.

In use, to treat the affected section of vertebrae, a medical practitioner obtains access to a surgical site including vertebrae in any appropriate manner, such as through incision and retraction of tissues. In some embodiments, spinal implant system 20 may be used in any existing surgical method or technique including open surgery, mini-open surgery, minimally invasive surgery and percutaneous surgical implantation, whereby vertebrae are accessed through a mini-incision, or sleeve that provides a protected passageway to the area. Once access to the surgical site is obtained, corpectomy is performed for treating the spine disorder. The diseased and/or damaged portion of vertebrae, and diseased and/or damaged intervertebral discs are removed to create a vertebral space.

A preparation instrument is employed to remove disc tissue, fluids, adjacent tissues and/or bone, and scrape and/or remove tissue from a vertebral surface of a superior vertebra and/or a vertebral surface of an inferior vertebra. Implant 22 may be provided with at least one agent, similar to those described herein, to promote new bone growth and fusion to treat the affected section of vertebrae. The components of spinal implant system 20 may be completely or partially revised, removed or replaced. In some embodiments, implant 22 is employed to stabilize vertebrae as a pre-assembled device or can be assembled in situ.

In some embodiments, implant 22 is inserted into a vertebral space via a posterior approach, with implant 22 in the collapsed or non-expanded orientation, shown in FIG. 3. Implant 22 is then moved from the collapsed or non-expanded orientation, shown in FIG. 3, to the expanded orientation, shown in FIG. 4. When implant 22 is in the expanded orientation, implant 22 has an increased height defined by the distance between an outer surface of end plate 60 and an opposite outer surface of end plate 86. Increasing the height of implant 22 moves implant 22 such that the outer surface of plate 60 engages a superior vertebra and the outer surface of end plate 86 engages an inferior vertebra such that implant 22 pushes the inferior vertebra away from the superior vertebra. In some embodiments, a material, such as, for example, bone graft material is inserted into implant 22. In some embodiments, implant 22 includes lateral portals for introducing graft in through the side rather than requiring it to go in from the ends. In some embodiments, implant 22 is loaded with bone graft material from the end on the back table prior to being implanted, and is then loaded with more bone graft material through the lateral portals after implantation.

In some embodiments, implant 22 may include fastening elements, which may include locking structure, configured for fixation with vertebrae to secure joint surfaces and provide complementary stabilization and immobilization to a vertebral region. In some embodiments, locking structure may include fastening elements such as, for example, rods, plates, clips, hooks, adhesives and/or flanges. In some embodiments, spinal implant system 20 can be used with screws to enhance fixation. In some embodiments, spinal implant system 20 and any screws and attachments may be coated with an agent, similar to those described herein, for enhanced bony fixation to a treated area. The components of spinal implant system 20 can be made of radiolucent materials such as polymers. Radiomarkers may be included for identification under x-ray, fluoroscopy, CT or other imaging techniques.

In some embodiments, implant 22 is inserted into a vertebral space via a posterior approach, with implant 22 in the expanded orientation, shown in FIG. 4, such that the outer surface of plate 60 engages a superior vertebra and the outer surface of end plate 86 engages an inferior vertebra. Implant 22 is then moved from the expanded orientation, shown in FIG. 4 to the collapsed or non-expanded orientation, shown in FIG. 3. As implant 22 moves from the expanded orientation to the collapsed or non-expanded orientation, implant 22 pulls the inferior vertebra toward the superior vertebra.

In some embodiments, the use of microsurgical and image guided technologies may be employed to access, view and repair spinal deterioration or damage, with the aid of spinal implant system 20. Upon completion of the procedure, the non-implanted components, surgical instruments and assemblies of spinal implant system 20 are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant system comprising:
   a first member extending along a longitudinal axis between opposite first and second ends, the first member being curved along the longitudinal axis from the first end to the second end, the first member comprising an inner surface, the inner surface defining a bore and a first thread;
   a second member comprising opposite proximal and distal ends, the second member being curved from the proximal end to the distal end, the distal end being positioned in the bore, the proximal end comprising an end plate, the second member comprising a second thread engaged with the first thread, the second thread comprising a series of gear teeth;
   a third member comprising opposite proximal and distal ends, the third member being curved from the proximal end of the third member to the distal end of the third member, the proximal end of the third member being positioned in the bore, the distal end of the third member comprising an end plate; and
   a driver comprising a gear configured to engage the gear teeth such that rotation of the driver relative to the first member and the second member rotates the second member relative to the first member to translate the second member relative to the first member along the longitudinal axis.

2. The spinal implant system recited in claim 1, wherein the third member is configured to translate relative to the first member along the longitudinal axis.

3. The spinal implant system recited in claim 1, further comprising a collar positioned about a sleeve of the third member, the collar comprising a third thread, the sleeve comprising a fourth thread engaged with the third thread, the fourth thread comprising a series of gear teeth configured to engage the gear such that rotation of the driver relative to the collar and the third member rotates the collar relative to the third member to translate the collar relative to the third member along the longitudinal axis.

4. The spinal implant system recited in claim 3, wherein the collar is removably coupled to the first member such that translation of the collar relative to the third member along the longitudinal axis translates the first member relative to the third member along the longitudinal axis.

5. The spinal implant system recited in claim 3, wherein the collar is monolithically formed with the first member such that translation of the collar relative to the third member along the longitudinal axis translates the first member relative to the third member along the longitudinal axis.

6. The spinal implant system recited in claim 3, wherein the collar is positioned between the end plate of the third member and the first member.

7. The spinal implant system recited in claim 3, wherein the first end includes a proximal end surface and the second end includes a distal end surface opposite the proximal end surface, a top surface of the collar directly engaging the distal end surface.

8. The spinal implant system recited in claim 3, wherein the longitudinal axis is a first longitudinal axis, the third member extending along a second longitudinal axis from the proximal end of the third member to the distal end of the third member, the third member bending along the second longitudinal axis as the collar translates relative to the third member along the first longitudinal axis.

9. The spinal implant system recited in claim 3, wherein the longitudinal axis is a first longitudinal axis, the third member extending along a second longitudinal axis from the proximal end of the third member to the distal end of the third member, the third member moving from a first orientation to a second orientation as the collar translates relative to the third member along the first longitudinal axis, the collar having a first radius of curvature when the third member is in the first orientation and a second radius of curvature when the third member is in the second orientation, the second radius of curvature being different than the first radius of curvature.

10. The spinal implant system recited in claim 3, wherein the second member and the collar each include an anterior end and an opposite posterior end, the anterior end of the second member being continuous with the anterior end of the collar, the posterior end of the second member being continuous with the posterior end of the collar, the anterior ends each being convexly curved, the posterior ends each being concavely curved.

11. The spinal implant system recited in claim 3, wherein the second member and the collar each include an anterior end and an opposite posterior end, the anterior end of the second member being continuous with the anterior end of the collar, the posterior end of the second member being continuous with the posterior end of the collar, the anterior end of the second member and the posterior end of the collar each being convexly curved, the posterior end of the second member and the anterior end of the collar each being concavely curved.

12. The spinal implant system recited in claim 3, wherein the second member and the collar each include an anterior end and an opposite posterior end, the anterior end of the second member being continuous with the anterior end of the collar, the posterior end of the second member being continuous with the posterior end of the collar, the anterior end of the second member and the posterior end of the collar each being concavely curved, the posterior end of the second member and the anterior end of the collar each being convexly curved.

13. The spinal implant system recited in claim 1, wherein the longitudinal axis is a first longitudinal axis, the end plate of the second member defining a second longitudinal axis, the second longitudinal axis extending at an acute angle relative to the first longitudinal axis as the second member translates relative to the first member along the first longitudinal axis.

14. The spinal implant system recited in claim 1, wherein the longitudinal axis is a first longitudinal axis, the end plate of the third member defining a second longitudinal axis, the second longitudinal axis extending at an acute angle relative to the first longitudinal axis as the second member translates relative to the first member along the first longitudinal axis.

15. The spinal implant system recited in claim 1, wherein the longitudinal axis is a first longitudinal axis, the second member extending along a second longitudinal axis from the proximal end of the second member to the distal end of the second member, the second member bending along the second longitudinal axis as the second member translates relative to the first member along the first longitudinal axis.

16. The spinal implant system recited in claim 1, wherein the longitudinal axis is a first longitudinal axis, the second member extending along a second longitudinal axis from the proximal end of the second member to the distal end of the second member, the second member moving from a first orientation to a second orientation as the second member translates relative to the first member along the first longitudinal axis, the second member having a first radius of curvature when the second member is in the first orientation and a second radius of curvature when the second member is in the second orientation, the second radius of curvature being different than the first radius of curvature.

17. The spinal implant system recited in claim 1, wherein the second member includes a first passageway extending through the end plate of the second member, the third member including a second passageway extending through the end plate of the third member, the passageways each being in communication with the bore.

18. The spinal implant system recited in claim 1, wherein the third member moves between a first orientation in which the proximal end of the third member is positioned within the second member and a second orientation in which the third member is spaced apart from the second member as the second member translates relative to the first member along the longitudinal axis.

19. A spinal implant system comprising:
  a first member extending along a longitudinal axis between opposite first and second ends, the first member being curved along the longitudinal axis from the first end to the second end, the first member comprising an inner surface, the inner surface defining a bore and a first thread;
  a second member comprising opposite proximal and distal ends, the second member being curved from the proximal end to the distal end, the distal end being positioned in the bore, the proximal end comprising an end plate, the second member comprising a second thread engaged with the first thread, the second thread comprising a series of gear teeth;
  a third member comprising opposite proximal and distal ends, the third member being curved from the proximal end of the third member to the distal end of the third member, the proximal end of the third member being positioned in the bore, the distal end of the third member comprising an end plate;
  a driver comprising a gear configured to engage the gear teeth such that rotation of the driver relative to the first member and the second member rotates the second member relative to the first member to translate the second member relative to the first member along the longitudinal axis; and a collar positioned about a sleeve of the third member, the collar comprising a third thread, the sleeve comprising a fourth thread engaged with the third thread, the fourth thread comprising a series of gear teeth configured to engage the gear such that rotation of the driver relative to the collar and the third member rotates the collar relative to the third member to translate the collar relative to the third member along the longitudinal axis, wherein the third member moves between a first orientation in which the proximal end of the third member is positioned within the second member and a second orientation in which the third member is spaced apart from the second member as the second member translates relative to the first member along the longitudinal axis.

20. A spinal implant system comprising:
a first member extending along a longitudinal axis between opposite first and second ends, the first member being curved along the longitudinal axis from the first end to the second end, the first member comprising an inner surface, the inner surface defining a bore and a first thread;
a second member comprising opposite proximal and distal ends, the second member being curved from the proximal end to the distal end, the distal end being positioned in the bore, the proximal end comprising an end plate, the second member comprising a second thread engaged with the first thread, the second thread comprising a series of gear teeth;
a third member comprising opposite proximal and distal ends, the third member being curved from the proximal end of the third member to the distal end of the third member, the proximal end of the third member being positioned in the bore, the distal end of the third member comprising an end plate;
a driver comprising a gear configured to engage the gear teeth such that rotation of the driver relative to the first member and the second member rotates the second member relative to the first member to translate the second member relative to the first member along the longitudinal axis; and a collar positioned about a sleeve of the third member, the collar comprising a third thread, the sleeve comprising a fourth thread engaged with the third thread, the fourth thread comprising a series of gear teeth configured to engage the gear such that rotation of the driver relative to the collar and the third member rotates the collar relative to the third member to translate the collar relative to the third member along the longitudinal axis, wherein the longitudinal axis is a first longitudinal axis, the third member extending along a second longitudinal axis from the proximal end of the third member to the distal end of the third member, the third member moving from a first orientation to a second orientation as the collar translates relative to the third member along the first longitudinal axis, the collar having a first radius of curvature when the third member is in the first orientation and a second radius of curvature when the third member is in the second orientation, the second radius of curvature being different than the first radius of curvature, and wherein the second member extends along a third longitudinal axis from the proximal end of the second member to the distal end of the second member, the second member moving from a third orientation to a fourth orientation as the second member translates relative to the first member along the first longitudinal axis, the second member having a third radius of curvature when the second member is in the third orientation and a fourth radius of curvature when the second member is in the fourth orientation, the fourth radius of curvature being different than the third radius of curvature.

* * * * *